United States Patent [19]

Deboeck et al.

[11] Patent Number: 5,036,100
[45] Date of Patent: Jul. 30, 1991

[54] PHARMACEUTICAL METHOD AND PREPARATION CONTAINING INDOMETHACIN

[75] Inventors: Arthur M. Deboeck, Gurabo, P.R.; Philippe R. Baudier, Waterloo, Belgium; Jacques J. Fossion, Braine-L'Alleud, Belgium; Paul J. Maes, Vise, Belgium

[73] Assignee: Pharlyse S.A. Societe Anonyme, Luxembourg, Belgium

[21] Appl. No.: 418,756

[22] Filed: Oct. 5, 1989

Related U.S. Application Data

[63] Continuation of Ser. No. 166,937, Mar. 11, 1988, abandoned.

[30] Foreign Application Priority Data

Mar. 13, 1987 [BE] Belgium ............................. 08700257

[51] Int. Cl.$^5$ ....................... A61K 31/36; A61K 31/40
[52] U.S. Cl. ...................................... 514/420; 514/464
[58] Field of Search ................................. 514/420, 464

[56] References Cited

U.S. PATENT DOCUMENTS 4,082,881  4/1978  Chen et al. ........................... 514/171
4,711,904  12/1987  Luzzi et al. .......................... 514/464

OTHER PUBLICATIONS

Chem. Abst. 99-164024f (1983) and 105-66482b (1986).

Primary Examiner—Stanley J. Friedman
Attorney, Agent, or Firm—Scrivener and Clarke

[57] ABSTRACT

This invention relates to a liquid pharmaceutical preparation for topical use on the skin of patients, said preparation containing indomethacin as active ingredient and dimethylisosorbide and isopropanol as excipients.

The preparation according to the invention allows an easy and precise local administration by external application on the skin of a solution of indomethacin in the excipients.

6 Claims, No Drawings

PHARMACEUTICAL METHOD AND PREPARATION CONTAINING INDOMETHACIN

This is a continuation of application Ser. No. 07/166,937 filed Mar. 11, 1988, now abandoned.

THE PRIOR ART

Among all the organs of the human body, the skin is the most accessible and extensive. Having a thickness of a few tenths of millimeter, the skin acts as a very efficient barrier against physical attacks and chemical agents. Since several centuries, many attempts have been made for treating topically body diseases, but a few positive results have only been obtained since a few decades.

Particularly, in the field of inflammatory diseases, numerous treatments through the skin have been tried, for example, by means of product containing rubefacients. The latter cause a superficial feeling of warmth due to a local vasodilatation, but cause no decrease or only a small decrease of inflammation or pain. More recently, topical preparations containing corticosteroids or non-steroid antiinflammatory agents appeared on the market.

The local treatment of inflammatory musculo-keletal affections is very interesting, since the pain is located in most cases in limited areas. An obvious psychological advantage of this type of treatment is that the painful area itself is treated and another advantage is that the oral administration may be avoided, so that it is possible to reduce and even to avoid completely the important systemic secondary effects which are important and frequently due to this type of drug, such as, for example, gastro-intestinal disorders.

Indomethacin or 1-(p-chlorobenzoyl)-5-methoxy-2-methylindole-3-acetic acid is a well known therapeutic substance having remarkable antiinflammatory and analgesic properties. In the class of the non-steroid antiinflammatory products, indomethacin is one of the most active and studied product, so that it is a drug of first choice for the treatment of said inflammatory diseases.

However indomethacin, when orally administered, has frequently important secondary effects such as irritations of the digestive mucosas which can finally cause simple or hemorrhagic gastritis and even gastrointestinal ulcers.

From these drawbacks, it is easy to understand the importance of finding other ways of administration avoiding the presence of indomethacin in the gastrointestinal tract.

A cutaneous topical preparation must not only have excellent properties of penetration of the drug into the painful area, but must also be devoid of a cutaneous reaction due to intolerance and must also be easily applicable.

At the present time, the physicians can use a topical indomethacin preparation in the form of an ointment or a gel. Although such a type of preparation is certainly therapeutically active, it has the following disadvantages. On the one hand, it cannot be applied in an accurate manner and, on the other hand, it is frequently advisable, when such a type of preparation is used, to cover the application area by means of a dressing or bandage, so as to avoid a staining of the garments which may be in contact with said area.

A liquid topical indomethacin-containing product to be used as a spray (LUIFLEX®) has recently appeared on the market. Although this liquid form permits an easy and precise application of the drug, while avoiding substantially the dangers of staining the garments, said liquid preparation does not possess the required qualities. As will be shown, this liquid preparation suffers not only from a lack of effectiveness, but it causes also important cutaneous intolerances.

DESCRIPTION OF THE INVENTION

This invention relates to a new indomethacin containing pharmaceutical preparation consisting essentially in a solution of indomethacin in a mixture of dimethylisosorbide and isopropanol.

Dimethylisosorbide is 1,4:3,6-dianhydro-2,5-di-o-methyl-D-glucitol (Atlas G-100, manufactured by ICI, Great Britain).

The new preparation according to this invention allows to the indomethacin to reach the heart itself of the inflammation through the skin without secondary cutaneous reactions of intolerance.

The pharmaceutical preparation according to this invention contains preferably about 0.5 to 15 grams of indomethacin, about 1 to 30 grams of dimethylisosorbide and a sufficient amount of isopropanol for a total weight of 100 grams.

The new pharmaceutical solution may be contained in a spray dispenser equipped with a valve which delivers each time a known and precise predetermined amount of the solution, i.e. a metering valve.

Said valve is preferably of the auto-priming pump type, so that, as already pointed out, the amount of sprayed liquid is accurate, without the need of using a propelling gas. The amount of liquid sprayed by the metering valve may vary from about 10 to 300 microliters.

EXAMPLES

Illustrative examples of the preparation and conditioning of the new galenic preparation according to the invention are given hereafter.

EXAMPLE 1

Indomethacin: 5 grams
Dimethylisosorbide: 18.5 grams
Isopropanol q.s.p.: 100 grams When the amount of indomethacin is mixed with the dimethylisosorbide and the half of the amount of isopropanol, the mixture is slightly heated and stirred until a clear or limpid solution is obtained. The remaining amount of isopropanol is then added and homogenized.

EXAMPLE 2

Indomethacin: 5 grams
Dimethylisosorbide: 12.5 grams
Stearylic ether of polyoxypropylene 15: 12.5 grams
Isopropanol q.s.p.: 100 grams

EXAMPLE OF CONDITIONING

The solution according to Example 1 or 2 is divided in fractions of 25 milliliters which are poured into aluminum bottles. These bottles are closed by crimpring on the neck of the bottles a metal ring provided with a metering valve which delivers a predetermined amount of solution each time that a pressure is applied on a push button. By means of the so-obtained conditioned pharmaceutical preparation, it is possible to spray a predetermined known and precise amount of indomethacin onto the skin surface to be treated.

A. Study of the anti-oedematous activity

The following pharmacological test shows objectively the effectiveness of the tested pharmaceutical preparations.

The study is performed with rats using the well-known carrageenin oedema test.

Thirty minutes before the induction of the inflammatory reaction, the hind right paw of the animals is immersed into the solution to be tested for one minute. The inflammatory reaction is started by injecting 0.1 milliliter of a physiological solution containing 1 % of carrageenin into the sub-aponeurotic area of the plantar arch.

| Influence of the various treatments of the carrageenin oedema development (number of animals = 6) | |
|---|---|
| Tested product | % increase of paw volume (average) |
| Control | 54 ± 2 |
| Placebo (excipients alone) | 47 ± 3 |
| Example 1 | 33 ± 3 |
| Example 2 | 37 ± 2 |
| Known product * | 40 ± 3 |

* LUIFLEX ® containing 1 gram of indomethacin, isopropylmyristate, perfume and isopropanol q.s.p. 100 grams.

The results of these tests show clearly that the indomethacin has, when administered locally, a protecting effect against an acute inflammatory reaction.

The preparation containing dimethylisosorbide of Example 1 according to the invention has given the largest protection against the oedema.

A statistically significant difference [t-test of STUDENT (see: SNEDECOR W. G. and COCHRAN G. W.: Statistical Methods (Iowa University Press, 1967, 6th edition); SPIEGEL M. R.: Theory and Problems of Statistics (Schaum's collection, N.Y.))] at the $p<0.01$ level has been found between the preparation of Example 1 and the known product.

It can thus be stated that the pharmaceutical preparation of Example 1, according to the invention, has a therapeutic activity which is substantially better than that of the known product existing presently on the market.

B. Study of the cutaneous tolerance

The used method was the "Methode officielle pour l'appreciation de l'agressivite superficielle cutanee par applications iteratives" (Official method for evaluating the cutaneous surface agressiveness by repeated applications) (Journal Officiel de la Republique Francaise of Apr. 21, 1976).

This method is used for evaluating the effect on the skin of a daily application of a product during several days. Albino rabbits are used and the products to be tested are applied onto the back and the flank previously sheared with an electric shearing machine; a small area of the hind-quarter of the animals, which has also been sheared, does not received any product and is used as control.

The absence or the presence of erythema and oedema is regularly noted and a numeral value on a scale from 0 to 4 is respectively given therefor (0=absence of erythema or oedema, 4=severe erythema or severe oedema). When each observation is carried out, the agressiveness index is calculated by adding the numeral values of the two scales and by dividing the result by the total number of evaluations of the intolerance phenomena. The meaning of the obtained agressiveness indexes is as follows:

Non-irritant: index lower than or equal to 0.5;
Slightly irritant: index comprised between 0.5 and 2;
Irritant: index comprised between 2 and 5;
Very irritant: index comprised between 5 and 8.

It is to be noted that the obtained index cannot mathematically be higher than 8.

The following results calculated after one month of application of the product have been obtained:

| Results of the cutaneous tolerance tests | | |
|---|---|---|
| Tested preparation | Indexes after one month | Meaning |
| Placebo | 0 | non-irritant |
| Example 1 | 0 | non-irritant |
| Known product * | 2.4 | irritant |

* LUIFLEX ®

The excipients contained in said known product and in the product according to Example 1 (according to the invention) differ only by the replacement of isopropyl myristate by dimethylisosorbide.

The isopropyl myristate, used in the LUIFLEX ® product, is known and described as a substance frequently used in the preparations intended to be applied on the skin, due to its lack of irritant and sensitizing properties (British Pharmaceutical Codex, 1973).

It is therefore very surprising to find that isopropyl myristate is the cause of irritant properties discovered in said known product, due to the fact that, when the isopropyl myristate is replaced by dimethylisosorbide, the irritant properties completely disappear.

This fact is the more unexpected as the preparation of Example 1 contains about four times more indomethacin (in percent) than the known product and as indomethacin can itself create cutaneous irritations, due to its acidic character.

From the results of all of these tests, it may be concluded that the preparation of Example 1 has not only a higher activity, but also unexpected and surprising properties of perfect cutaneous tolerance.

What is claimed is:

1. The method of subcontaneously treating a region of inflammatory musculoskeletal affliction in patients suffering from such afflictions comprising applying directly to the skin of the patient over the region of the affliction a liquid preparation of about 5 to 15% by weight of indomethacin as the active ingredient of said preparation and, as excipient of said preparation a mixture of 1 to 3% by weight of dimethylisosorbide and 55 to 98.5% by weight of isopropanol, and allowing the preparation to pass through the skin and to the region of said affliction.

2. A liquid topical pharmaceutical preparation for the treatment of inflammatory musculo skeletal afflictions for application to the skin, comprising about 0.5 to 15% by weight of indomethacin as active ingredient and as excipients 1 to 30% by weight of dimethylisosorbide and 98.5 to 55% by weight of isopropanol.

3. A pharmaceutical preparation according to claim 2, which contains about 5 to 100 milligrams of indomethacin per gram of the preparation.

4. A pharmaceutical preparation according to claim 3, in which the concentration of indomethacin is of about 50 milligrams per gram of the preparation.

5. A pharmaceutical preparation according to claim 3, which contains from about 1 to 600 milligrams of dimethylisosorbide per gram of the preparation.

6. A pharmaceutical preparation according to claim 3, which contains from about 10 to 300 milligrams of dimethylisosorbide per gram of the preparation.

* * * * *

UNITED STATES PATENT AND TRADEMARK OFFICE
CERTIFICATE OF CORRECTION

PATENT NO. : 5,036,100

DATED : July 30, 1991

INVENTOR(S) : Arthur M. Deboeck et al.

It is certified that error appears in the above-identified patent and that said Letters Patent is hereby corrected as shown below:

On the Title page item:

[73] Assignee: Pharlyse S.A. Societe Anonyme, Luxembourg

Signed and Sealed this

Twenty-second Day of December, 1992

Attest:

DOUGLAS B. COMER

*Attesting Officer*     Acting Commissioner of Patents and Trademarks